United States Patent [19]
Hettiarachchi et al.

[11] Patent Number: 5,719,911
[45] Date of Patent: Feb. 17, 1998

[54] SYSTEM FOR MONITORING NOBLE METAL DISTRIBUTION IN REACTOR CIRCUIT DURING PLANT APPLICATION

[75] Inventors: Samson Hettiarachchi, Menlo Park; Robert Lee Cowan, II; Robert James Law, both of Livermore; Thomas Pompilio Diaz, San Martin, all of Calif.

[73] Assignee: General Electric Company, San Jose, Calif.

[21] Appl. No.: 791,369

[22] Filed: Jan. 30, 1997

Related U.S. Application Data

[60] Division of Ser. No. 482,243, Jun. 7, 1995, Pat. No. 5,625,656, which is a continuation-in-part of Ser. No. 209,572, Mar. 10, 1994, Pat. No. 5,600,691, which is a continuation-in-part of Ser. No. 143,513, Oct. 29, 1993, abandoned, and Ser. No. 143,514, Oct. 29, 1993, Pat. No. 5,448,605.

[51] Int. Cl.$^6$ .............. G21C 17/00; G01N 27/26
[52] U.S. Cl. .............. 376/245; 376/249; 376/259; 204/404; 204/435; 205/786
[58] Field of Search .............. 376/245, 247, 376/249, 259, 300, 301, 305, 306; 204/400, 404, 435, 433; 205/777, 786; 73/863.02, 863.23, 861, 861.08

[56] References Cited

U.S. PATENT DOCUMENTS

| | | | |
|---|---|---|---|
| 4,059,406 | 11/1977 | Fleet | 205/786 |
| 4,111,830 | 9/1978 | Bannister | 422/17 |
| 4,488,939 | 12/1984 | Fu | 205/777 |
| 4,759,902 | 7/1988 | Anstine | 376/306 |
| 5,130,080 | 7/1992 | Niedrach | 376/305 |
| 5,130,081 | 7/1992 | Niedrach | 376/305 |
| 5,135,709 | 8/1992 | Andresen et al. | 376/305 |
| 5,164,152 | 11/1992 | Kim et al. | 376/305 |
| 5,203,984 | 4/1993 | Sakai et al. | 204/435 |
| 5,316,633 | 5/1994 | Sakai et al. | 376/245 X |
| 5,353,650 | 10/1994 | Barshay et al. | 73/863.02 |
| 5,398,268 | 3/1995 | Ibe et al. | 376/305 |
| 5,465,278 | 11/1995 | Cowan, II et al. | 376/245 |
| 5,465,281 | 11/1995 | Andresen et al. | 376/305 |

FOREIGN PATENT DOCUMENTS

| | | |
|---|---|---|
| 0265723 | 5/1988 | European Pat. Off. . |
| 0526160 | 2/1993 | European Pat. Off. . |
| 9218665 | 10/1992 | WIPO . |

OTHER PUBLICATIONS

Derwent Publications Ltd., London, GB; AN 84-059353 & JP-A-59 016 983 (Katayama Kagaku Kogyo Kenkyush), Abstract.

Primary Examiner—Michael J. Carone
Assistant Examiner—Matthew J. Lattig
Attorney, Agent, or Firm—James E. McGinness; Dennis M. Flaherty

[57] ABSTRACT

A system for ensuring the distribution of noble metal in the reactor circuit during plant application without measuring the reactor water for noble metal content by chemical analysis. The system performs the measurement of electrochemical corrosion potential in an autoclave or a high-flow test section that is connected to the reactor water circuit through sample lines downstream of the injection port, preferably the point in the reactor circuit which is furthest from the injection port. If the noble metal flows into the autoclave or test section at these distant points in the reactor circuit, then the noble metal will deposit on the test specimens inside the autoclave or test section. After the noble metal has been injected for a predetermined duration, the electrochemical corrosion potential autoclave or test section is exposed to hydrogen water chemistry conditions and the electrochemical corrosion potentials of the specimens inside the autoclave or test section will be measured to determine the extent of their catalytic response. A good catalytic response indicates that the noble metal has reached the locations upstream where electrochemical corrosion potential is being measured.

14 Claims, 4 Drawing Sheets

SYSTEM FOR MONITORING NOBLE METAL DISTRIBUTION IN REACTOR CIRCUIT DURING PLANT APPLICATION

RELATED PATENT APPLICATIONS

This application is a divisional application of U.S. patent application Ser. No. 08/482,243 filed on Jun. 7, 1995 and issued as U.S. Pat. No. 5,625,656, continuation-in-part application of U.S. patent ppplication Ser. No. 08/209,572 filed on Mar. 10, 1994 and issued as U.S. Pat. No. 5,600,691, which in turn is a continuation-in-part application of U.S. patent application Ser. No. 08/143,513, filed on Oct. 29, 1993 and abandoned, and application Ser. No. 08/143,514, filed on Oct. 29, 1993 and issued as U.S. Pat. No. 5,448,605.

FIELD OF THE INVENTION

This invention relates to reducing the corrosion potential of components exposed to high-temperature water. As used herein, the term "high-temperature water" means water having a temperature of about 150° C. or greater or steam. High-temperature water can be found in a variety of known apparatus, such as water deaerators, nuclear reactors, and steam-driven power plants.

BACKGROUND OF THE INVENTION

A light-water nuclear reactor has a core of nuclear fuel which is cooled by recirculating water. A reactor pressure vessel contains the reactor coolant, which is heated to high temperature by heat produced as a result of nuclear fission produced by the nuclear fuel. Piping circuits carry the heated water or steam to the steam generators or turbines and carry circulated water back to the vessel via feedwater after passing through the main condenser. Operating pressures and temperatures for the reactor pressure vessel are about 7 MPa and 288° C. for a boiling water reactor (BWR), and about 15 MPa and 320° C. for a pressurized water reactor (PWR). The materials used in both BWRs and PWRs must withstand various loading, environmental and radiation conditions.

Some of the materials exposed to high-temperature water include carbon steel, alloy steel, stainless steel, and nickel-based, cobalt-based and zirconium-based alloys. Despite careful selection and treatment of these materials for use in water reactors, corrosion occurs on the materials exposed to the high-temperature water. Such corrosion contributes to a variety of problems, e.g., stress corrosion cracking, crevice corrosion, erosion corrosion, sticking of pressure relief valves and buildup of the gamma radiation-emitting Co-60 isotope.

Stress corrosion cracking (SCC) is a known phenomenon occurring in reactor components, such as structural members, piping, fasteners, and welds, exposed to high-temperature water. As used herein, SCC refers to cracking propagated by static or dynamic tensile stressing in combination with corrosion at the crack tip. The reactor components are subject to a variety of stresses associated with, e.g., differences in thermal expansion, the operating pressure needed for the containment of the reactor cooling water, and other sources such as residual stress from welding, cold working and other asymmetric metal treatments. In addition, water chemistry, welding, heat treatment, and radiation can increase the susceptibility of metal in a component to SCC.

It is well known that SCC occurs at higher rates when oxygen is present in the reactor water in concentrations of about 5 ppb or greater. SCC is further increased in a high radiation flux where oxidizing species, such as oxygen, hydrogen peroxide, and short-lived radicals, are produced from radiolytic decomposition of the reactor water. Such oxidizing species increase the electrochemical corrosion potential (ECP) of metals. Electrochemical corrosion is caused by a flow of electrons from anodic to cathodic areas on metallic surfaces. The ECP is a measure of the kinetic tendency for corrosion phenomena to occur, and is a fundamental parameter in determining rates of, e.g., SCC, corrosion fatigue, corrosion film thickening, and general corrosion.

In a BWR, the radiolysis of the primary water coolant in the reactor core causes the net decomposition of a small fraction of the water to the chemical products $H_2$, $H_2O_2$, $O_2$ and oxidizing and reducing radicals. For steady-state operating conditions, equilibrium concentrations of $O_2$, $H_2O_2$, and $H_2$ are established in both the water which is recirculated and the steam going to the turbine. This concentration of $O_2$, $H_2O_2$, and $H_2$ is oxidizing and results in conditions that can promote intergranular stress corrosion cracking (IGSCC) of susceptible materials of construction.

IGSCC proceeds at an accelerated rate in systems in which the ECP is above the critical potential, and at a substantially lower or zero rate in systems in which the ECP is below the critical potential. As used herein, the term "critical potential" means a corrosion potential at or below a range of values of about −230 to −300 mV based on the standard hydrogen electrode (SHE) scale. Water containing oxidizing species such as oxygen increases the ECP of metals exposed to the water above the critical potential, whereas water with little or no oxidizing species present results in an ECP below the critical potential. Thus, susceptibility to SCC in BWRs is highly influenced by corrosion potential. Reduction of the corrosion potential is the most widely pursued approach for mitigating SCC in existing boiling water reactor power plants.

One method employed to mitigate IGSCC of susceptible material is the application of hydrogen water chemistry (HWC), whereby the oxidizing nature of the BWR environment is modified to a more reducing condition. This effect is achieved by adding hydrogen gas to the reactor feedwater. When the hydrogen reaches the reactor vessel, it reacts with the radiolytically formed oxidizing species on metal surfaces to reform water, thereby lowering the concentration of dissolved oxidizing species in the water in the vicinity of metal surfaces. The rate of these recombination reactions is dependent on local radiation fields, water flow rates and other variables.

The injected hydrogen reduces the level of oxidizing species in the water, such as dissolved oxygen and hydrogen peroxide, and as a result lowers the ECP of metals in the water. However, factors such as variations in water flow rates, reactor power and the time or intensity of exposure to neutron or gamma radiation result in the production of oxidizing species at different levels in different reactors. Thus, varying amounts of hydrogen have been required to reduce the level of oxidizing species sufficiently to maintain the ECP below the critical potential required for protection from IGSCC in high-temperature water.

It has been shown that IGSCC of Type 304 stainless steel used in BWRs can be mitigated by reducing the ECP of the stainless steel to values below −0.230 V(SHE). However, high hydrogen additions, e.g., of about 1 ppm or greater into the feedwater, that may be required to reduce the ECP below the critical potential, can result in a higher radiation level in the steam-driven turbine section from incorporation of the short-lived N-16 species in the steam. Thus, recent investigations have focused on using minimum levels of hydrogen to achieve the benefits of HWC with minimum increase in the main steam radiation dose rates.

An effective approach to achieve this goal is to either coat or alloy the stainless steel surface with palladium or any other noble metal. As used herein, the term "noble metal" means metals taken from the group consisting of platinum, palladium, osmium, ruthenium, iridium, rhodium, and mixtures thereof. The presence of palladium on the stainless steel surface reduces the hydrogen demand to reach the required IGSCC critical potential of −0.230 V(SHE). Compared to the HWC technique, which employs large hydrogen additions to suppress and recombine oxygen and hydrogen peroxide formed by radiolysis to very low levels (e.g., <2 ppb), the noble metal approach requires only that sufficient hydrogen be present so that, as water is formed on the catalytic surface, all oxygen and hydrogen peroxide are consumed (e.g., $2H_2 + O_2 \rightarrow 2H_2O$). Additionally, lower potentials (generally the thermodynamic minimum) are obtained. Depending on the precise location within a BWR, the hydrogen addition required in the noble metal approach may be reduced by a factor of 5 to 100.

The development of techniques to apply noble metal in situ to all wetted components of a reactor represents a breakthrough in extending the applications of the noble metal technology, since manual application (e.g., by thermal spray or fusion cladding) requires complex tooling, is slow and expensive, and can only coat surfaces to which there is sufficiently good access.

U.S. patent application Ser. No. 08/143,513 discloses a technique to coat or dope oxidized stainless steel surfaces in situ by injecting a noble metal compound in the reactor circuit, which noble metal compound then releases species of the noble metal into high-temperature water. As used herein, the term "species" means atoms, ions and molecules. The compound is injected in situ in the form of a solution or a colloidal suspension. As used herein, the term "solution" means both solutions and colloidal suspensions.

The preferred noble metal compound is $Na_2Pt(OH)_6$. Another suitable compound for use in the invention is palladium acetylacetonate ($Pd(CH_3COCHCOCH_3)_2$), an organometallic compound, which undergoes thermal decomposition in high-temperature water, thereby releasing palladium atoms which deposit on oxidized surfaces. Alternatively, palladium nitrate, which releases palladium ions upon ionization in high-temperature water, can be used. As used herein, the term "release" also includes the colloidal formation of noble metal molecules. The concentration of noble metal in the reactor water is preferably in the range of 5 to 100 ppb. Doping occurs when noble metal atoms, ions or molecules (i.e., species) released into the high-temperature water deposit on the oxidized surfaces of the flooded reactor components. Other noble metal compounds of organic, organometallic or inorganic nature, as well as compounds of titanium, zirconium, molybdenum, niobium and tungsten can also be used. As used herein, the term "transition metals" means the group of metals consisting of titanium, zirconium, molybdenum, niobium and tungsten. Other suitable noble metal compounds are $K_3Rh(NO_2)_6$, $Pt(NH_3)_4(NO_2)_2$ and mixtures of $Na_2Pt(OH)_6$ and $K_3Rh(NO_2)_6$.

Following noble metal injection, hydrogen can be injected into the reactor water. As hydrogen is added, the potential of the noble metal-doped oxide film on the stainless steel components is reduced to values which are much more negative than when hydrogen is injected into a BWR having stainless steel components which are not doped with noble metal.

The surfaces inside the reactor which become doped with noble metal as a result of the foregoing treatment have catalytic properties. Once these surfaces are doped with noble metal, their ECPs remain low, i.e. below the threshold potential for IGSCC, e.g. <−0.230 V(SHE), in the presence of low concentrations of dissolved hydrogen. Numerous laboratory experiments have confirmed that doping of surfaces with noble metal prevents crack initiation and mitigates crack growth of the structural materials used in the nuclear reactor.

In the laboratory, noble metal doping is accomplished by injecting a solution of a noble metal compound into high-temperature water in a recirculating flow loop comprising a heated high-pressure vessel 10, e.g., an autoclave (see FIG. 1). The vessel has an inlet 12 and an outlet 14 which are in flow communication with a chamber 16 inside vessel 10. The matrix 18 to be coated or doped with noble metal is placed inside the vessel. The vessel inlet 12 is connected to an outlet at the bottom of a water tank 20 via a recirculation pump 22 and a heat exchanger 24. One or more gas bottles 34 is selectively in fluid communication with water tank 20 for dissolving one or more gases (e.g., hydrogen, oxygen and nitrogen) in the recirculating water to obtain the necessary water chemistry conditions. The vessel 10 has a heater capable of heating the water in chamber 16 to a temperature sufficient to cause thermal decomposition of a noble metal compound which is injected at injection point 26 located downstream of heat exchanger 24 directly into the heated high-pressure vessel 10. The heated water inside chamber 16 is returned to the water tank 20 via a heat exchanger 24, a backpressure regulator 28 and a water cleanup system 30. The heat exchanger transfers heat from the hot water exiting vessel 10 to the cold water entering vessel 10, whereby the incoming water is pre-heated. A chemical analysis system 32 may be used to sample the water exiting the vessel 10 and determine the chemical composition of the water by a conventional chemical analysis technique.

The concentration of the noble metal in the feed tank 20 is maintained such that after injection, the diluted water stream will have the desired concentration of the noble metal, generally in the range 10 to 100 ppb. The amount of noble metal entering the autoclave 10 is kept constant by maintaining both the concentration in the feed tank and the injection rate constant.

Attempts to measure the actual concentration of noble metal in the autoclave showed that the noble metal in the water sample was present in both ionic as well as non-ionic form. The non-ionic form is likely the result of the formation of colloids during dilution of the noble metal compound in the high-temperature water inside the autoclave. The formation of colloids also complicates the chemical analysis in that if agglomeration of colloidal particles occurs, the colloidal particles may tend to settle in the sampling bottle. Such particulate settling results in some errors, making analysis of noble metal during process application by conventional analytical means more difficult. Thus, alternative approaches to ensure the proper distribution of noble metal during plant application need to be developed to verify the final process application.

SUMMARY OF THE INVENTION

The present invention describes an alternative method of ensuring the distribution of noble metal in the reactor circuit during plant application without measuring the reactor water for noble metal content by chemical analysis. The method involves the in situ measurement of ECP in an autoclave or a high-flow test section that is connected to the reactor water circuit through sample lines downstream of the injection port, preferably at a point in the reactor circuit which is furthest from the injection port to ensure noble metal distribution over all wetted components of the reactor. If the noble metal flows into the monitoring autoclave or test section at these distant points in the reactor circuit, then the noble metal will deposit on the test specimens inside the autoclave or test section, as has been observed during laboratory tests.

After the noble metal has been injected for a predetermined duration, the ECP autoclave or test section is exposed to HWC conditions by injecting $H_2$-containing water into the test section while the reactor water continues to flow through and the ECPs of the specimens inside the autoclave or test section will be measured to determine the extent of their catalytic response. A good catalytic response indicates that the noble metal has reached the ECP measuring locations, providing evidence that the reactor surfaces upstream of that location should exhibit similar ECPs when exposed to HWC conditions. This verification method is a rapid and accurate on-line measure of the actual process application without using chemical analysis, which may take several hours to days to complete.

DETAILED DESCRIPTION OF THE PREFERRED EMBODIMENTS

Figure 1:
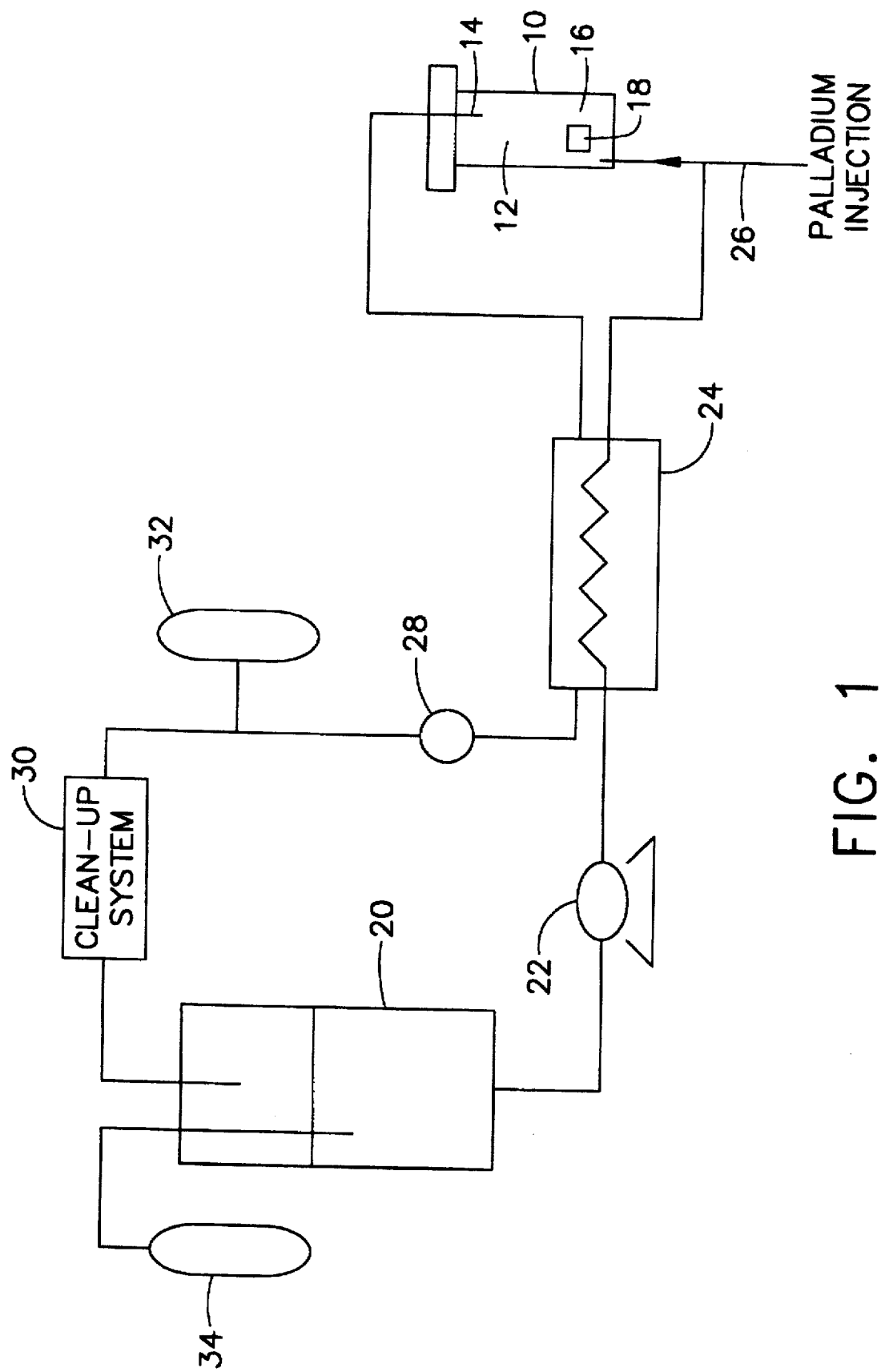
FIG. 1 is a block diagram showing a laboratory test arrangement for noble metal injection into high-temperature water.
Figure 2:
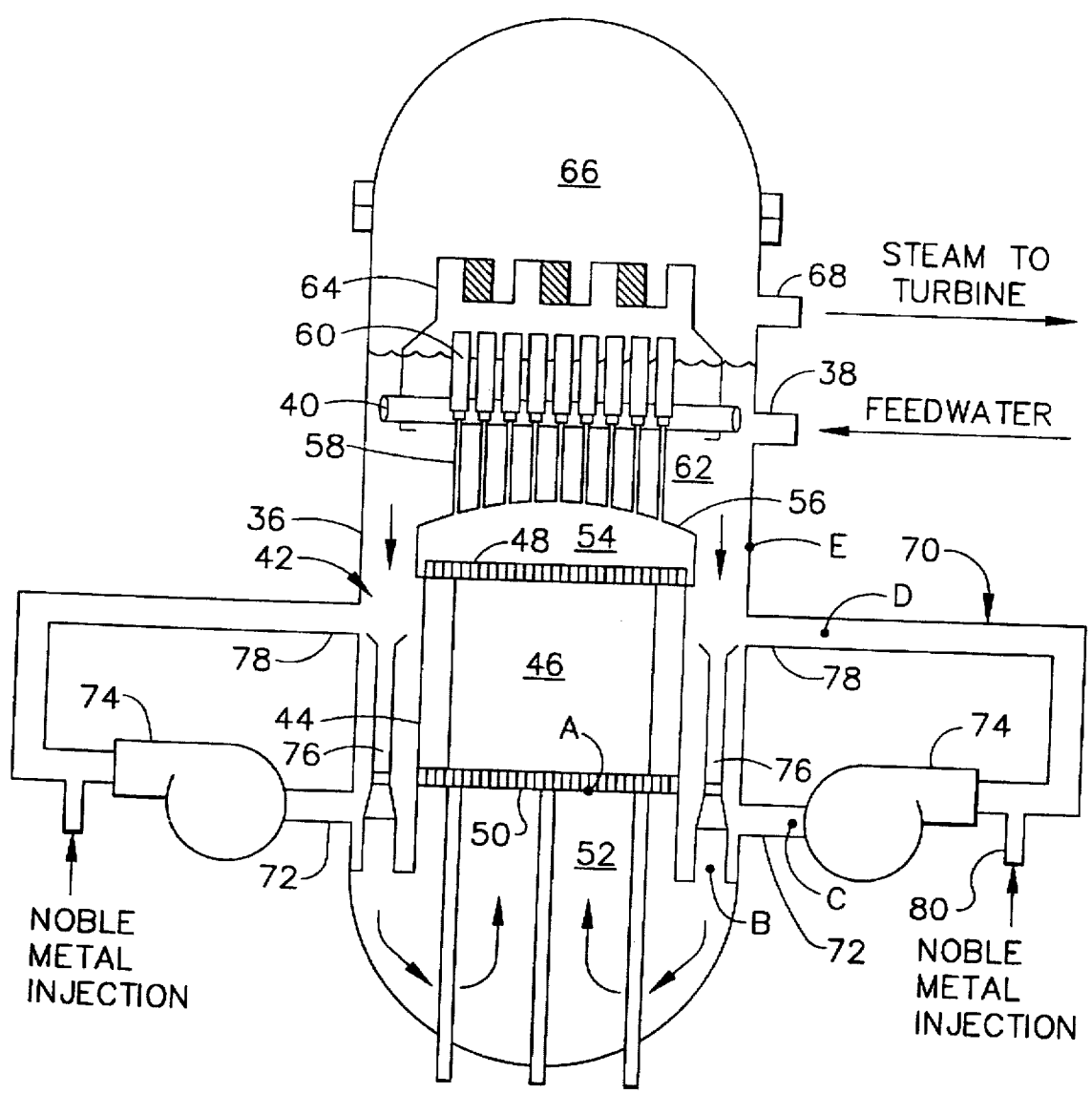
FIG. 2 is a schematic showing the noble metal injection and sampling locations in a reactor coolant circuit of a conventional BWR in accordance with the present invention.

The fluid flow in a BWR will be generally described with reference to FIG. 2. During BWR operation, feed-water is admitted into a reactor pressure vessel (RPV) 36 via a feedwater inlet 38 and a feedwater sparger 40. The feedwater sparger 40 is a ring-shaped pipe having suitable apertures for circumferentially distributing the feedwater inside the RPV. The feedwater from sparger 40 flows downwardly through the downcomer annulus 42, which is an annular region between RPV 36 and the core shroud 44. Core shroud 44 is a stainless steel cylinder which surrounds the core 46, which comprises numerous fuel assemblies (not shown). Each fuel assembly is supported at the top by top guide 48 and at the bottom by core support plate 50. Water flowing through downcomer annulus 42 then is recirculated through the recirculation piping system 70 via recirculation inlet 72 and recirculation pump 74 and fed to the jet pump assemblies 76 via the recirculation outlet 78. The jet pump assemblies then discharge water into the lower plenum 52. The water in the lower plenum, which is at relatively low pressure, flows upward into the fuel core 46. The nuclear heat generated by the core produces a boiling boundary layer, with a pressure difference (delta P) across the core support plate 50. A mixture of water and steam exits the core and enters upper plenum 54 under the shroud head dome 56. Upper plenum 54 provides standoff between the steam-water mixture exiting core 46 and entering vertical standpipes 58 disposed atop shroud head dome 56. The steam-water mixture flows through standpipes 58 and enters steam separators 60, which are of the axial-flow centrifugal type. The separated liquid water then mixes with feedwater in the mixing plenum 62, which mixture then returns to the downcomer annulus 42. The separated steam passes through steam dryers 64 and enters steam dome 66. The steam is withdrawn from the RPV via steam outlet 68.

To protect against stress corrosion cracking, the oxidized stainless steel surfaces inside the BWR can be doped with noble metal in situ by injecting a noble metal-containing compound into the high-temperature water of the BWR. Preferably the noble metal compound is injected at a point 80 (see FIG. 2) immediately downstream of each recirculation pump 74. The injected noble metal compound is carried by the recirculating water after passing through the lower plenum 52 and finally passes through the fuel core 46. The high temperatures as well as the gamma and neutron radiation in the reactor core cause the compound to release noble metal species which deposit on or incorporate in the wetted oxidized surfaces.

The present invention is a non-chemical analytical method of ensuring the distribution of injected noble metal to critical surfaces of the reactor circuit. For example, for the foregoing case where the noble metal compound is injected into the reactor water as a solution at point 80 downstream of the recirculation pumps 74, an ECP measurement system in accordance with the present invention will be installed at one or more of the sampling points A through E (see FIG. 2) located upstream of each recirculation pump. The preferred location is the pressure line upstream of the recirculation pump 74 (sampling point C in FIG. 2). The other sampling points are respectively located at the core delta P lines (A), the jet pump sensing line (B), the recirculation line downstream of the recirculation pump (D) and the downcomer annulus at the top guide elevation.

Each ECP measurement system will indicate whether the noble metal has reached the respective sampling point in the reactor coolant circuit. The ECP measurement system can be either an autoclave containing ECP specimens or a high flow test section containing appropriate test specimens. Each ECP measurement set-up will be plumbed into the respective sampling point via a respective sampling line. Each ECP measurement set-up will also have means for adding dissolved gas to the sampled water before it flows into the ECP specimen test section so that the chemistry of the sampled water diverted from the reactor circuit region can be changed from normal water chemistry to HWC without changing the water chemistry of the entire reactor circuit.

Figure 4:
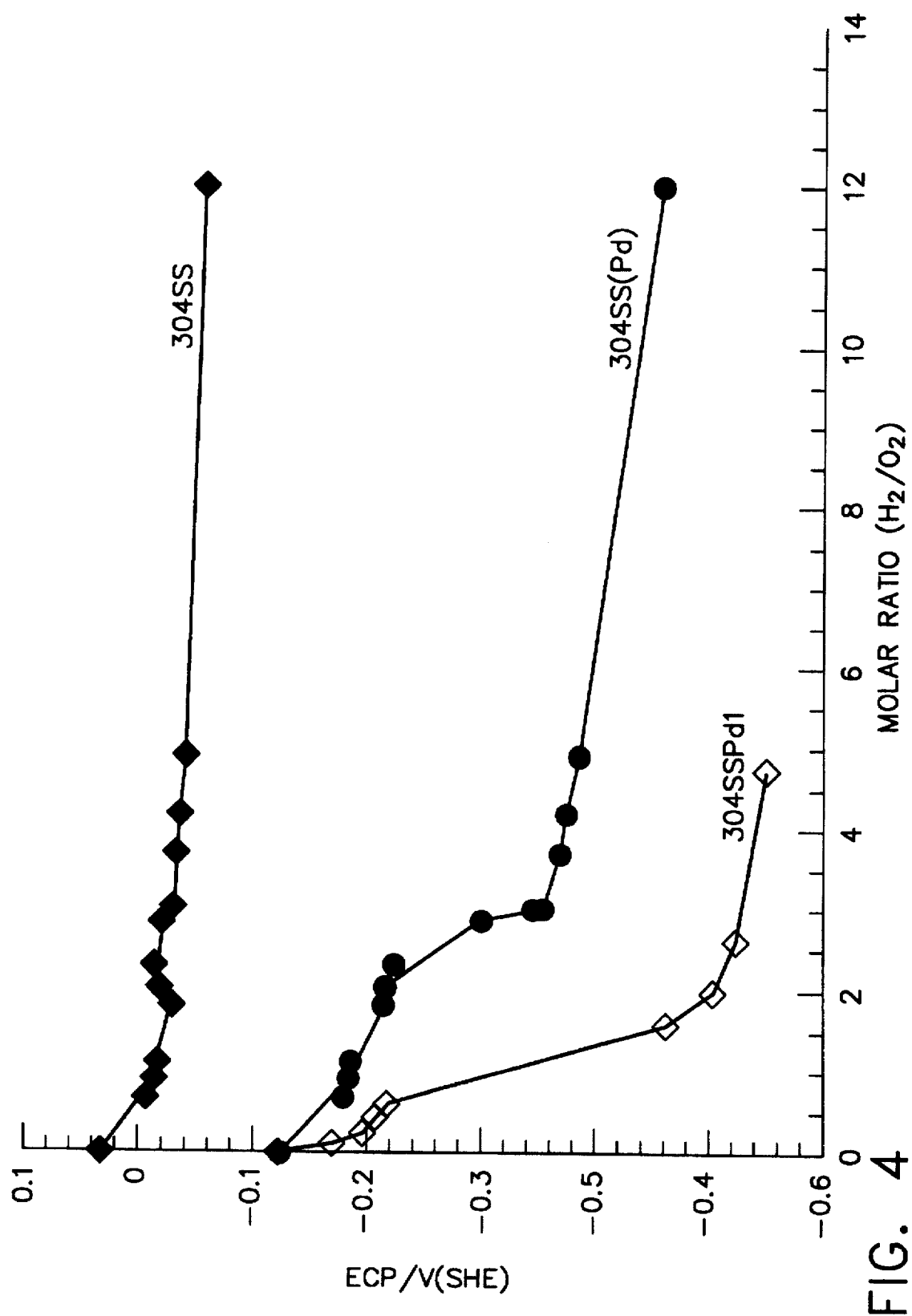
FIG. 4 is a plot showing the ECP response as a function of the molar ratio of hydrogen to oxygen for three Type 304 stainless steel specimens: 304SS—not doped with palladium; 304SS(Pd)—doped with 58 ppb Pd; and 304SSPd1—doped with 96 ppb Pd.

During the noble metal injection, each ECP measurement system will draw reactor water from a different part of the reactor circuit. The process will begin by injecting the desired concentration of noble metal into the reactor water at injection point 80 based on laboratory data. During this period, the ECP test sections will have the same water chemistry as the reactor water. After injecting the noble metal during a predetermined time interval, the water chemistry in the ECP test sections will be changed locally to HWC while monitoring the ECPs of the test specimens in the test section. If noble metal has gone through the reactor circuit and reached that location, then the specimens should respond to HWC by showing catalytic activity, as shown in FIG. 4. Thus, even though the noble metal content is not measured analytically, the ECP measurement provides firm evidence instantly that the noble metal has reached that location in the reactor circuit as a result of the injection process, confirming that the process application has been successfully completed. If the catalytic ECP response is not seen, this indicates that the noble metal injection should be continued. This method of process monitoring can be used even during the injection process from time to time to check whether the noble metal has reached that location. The monitoring process described herein can be used either as a stand-alone method or as a complementary method for the other, e.g., chemical, analytical methods.

An important advantage of the ECP monitoring method is that it is on-line and the result is instantaneous (e.g., a few seconds), whereas the analytical methods would take hours to days depending on the complexity of the sample preparation involved before analysis. Furthermore, even if the analytical method is rapid and successful, it only confirms that the noble metal got to that location. It gives no indication of whether the noble metal, in fact, has deposited on the surface, although based on laboratory data, the presence of noble metal in the water is a good indication of its presence on the adjacent metal surfaces. The ECP monitoring method of the present invention, on the other hand, shows no ambiguity in that it monitors the ECP of surfaces of that location and hence is a true measure of the catalytic activity of the surfaces. Furthermore, the catalytic ECP response of specimens in the test section is a clear confirmation of noble metal deposition on all surfaces upstream of the injection port.

Figure 3:
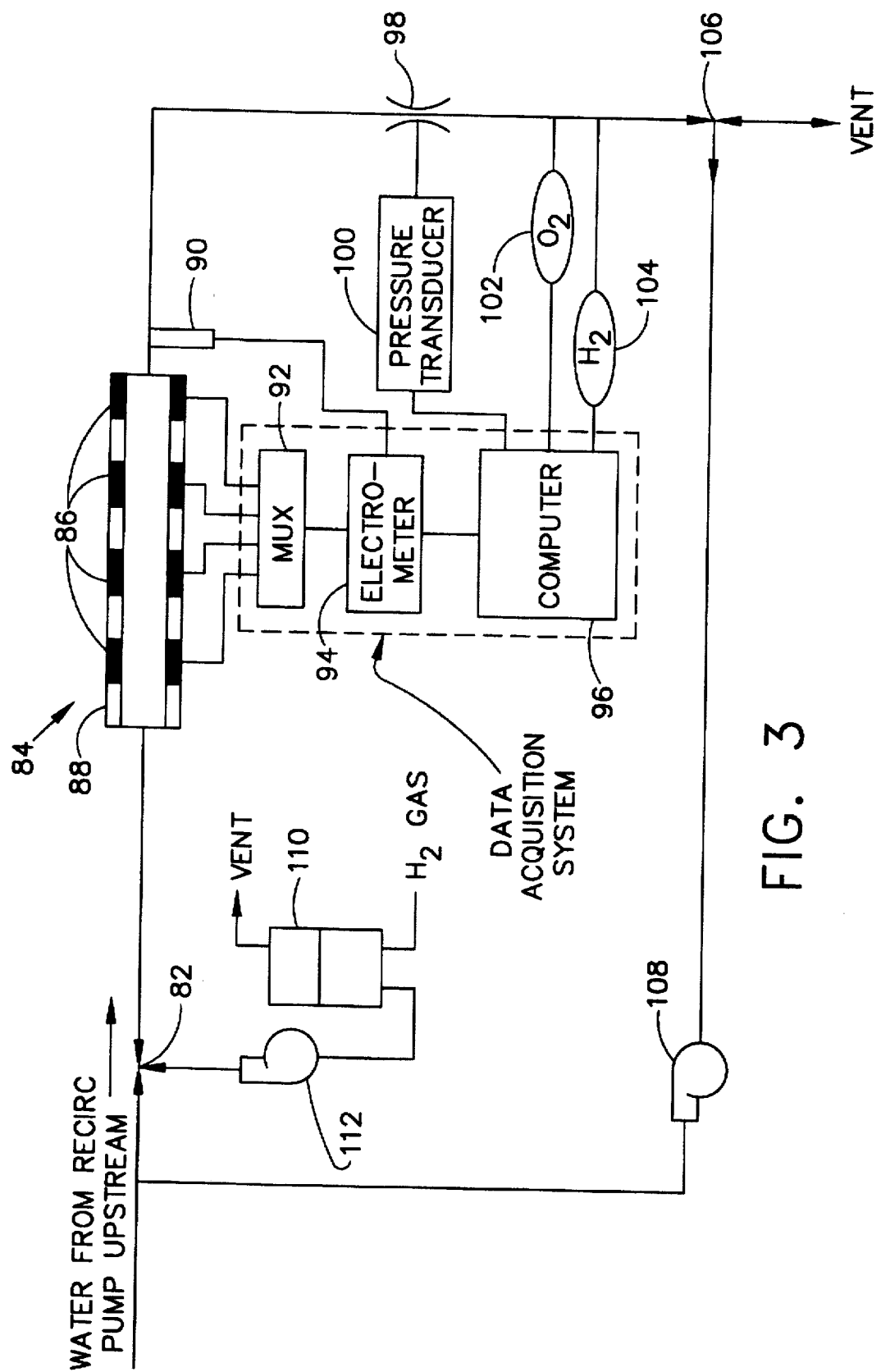
FIG. 3 is a block diagram showing an on-line ECP measurement set-up for monitoring noble metal distribution in accordance with a preferred embodiment of the invention.

The ECP measurement set-up in accordance with the preferred embodiment of the invention is shown in FIG. 3. A sample of water taken from the reactor circuit at one of the sampling points (e.g., sampling point C in FIG. 2) flows from the sampling line to an ECP specimen test section 84 via a three-way valve 82. The three-way valve 82 is also connected to an outlet of a pump 112 which can be selectively actuated to pump water from a water tank 110. Means are provided so that hydrogen gas can be bubbled into the water tank, with the excess being vented. A volume of water with dissolved hydrogen can be added to the sampled water via pump 112 and valve 82 so that the chemistry of the sampled water can be changed from normal water chemistry to HWC without changing the water chemistry of the entire reactor circuit.

The ECP specimen test section 84 comprises a plurality of well-oxidized stainless steel annular rings 86 arranged in sequence with electrically insulating annular rings 88 arranged between adjacent rings 86. Annular stainless steel rings 86 are insulated from each other as well as from any metal part in the test section. The rings 86 and 88 are connected in an alternating series to form a flow channel. A reference electrode 90 is arranged downstream of the outlet of test section 84. The ECP at the inner surface of each stainless steel ring 86 can be determined by measuring the difference between the potential at the inner surface of ring 86 and the potential at the surface of reference electrode 90 using an electrometer 94. The sampled water is flowing during the ECP measurement. The potential difference is measured for each stainless steel ring 86 sequentially by sampling the respective potentials of rings 86 using a multiplexer 92. The resulting ECP values are stored and displayed by a computer 96. The multiplexer 92, electrometer 94 and computer 96, along with a monitor (not shown), constitute the data acquisition system.

After exiting the ECP specimen test section 84, the sampled water flows through a flow venturi 98. A pressure transducer 100 measures the pressure drop across the venturi and outputs an electrical signal to the computer 96 for processing. The pressure drop is calibrated to give flow velocity. The computer correlates the pressure values with the corresponding measured ECPs, which are a function of flow velocity. The degree to which valve 106 is opened can be used to set the flow velocity to a value corresponding to the flow velocity in the reactor circuit portion being monitored. In addition, the dissolved oxygen and dissolved hydrogen levels are detected using oxygen sensor 102 and hydrogen sensor 104 respectively. The sensor outputs are also input to the computer, which will control the flow through pump 112 to maintain the desired $H_2/O_2$ molar ratio in excess of 2.

The water sample can then be vented via three-way valve 106. Alternatively, the water sample can be recycled back into the reactor circuit via valve 106 and pump 108.

The foregoing method has been disclosed for the purpose of illustration. Variations and modifications of the disclosed method will be readily apparent to practitioners skilled in the art. All such variations and modifications are intended to be encompassed by the claims set forth hereinafter.

We claim:

1. A system for measuring electrochemical corrosion potential comprising an inlet pipe, an outlet pipe, a ring electrode having a channel with an inlet in flow communication with said inlet pipe and an outlet in flow communication with said outlet pipe so that fluid flowing from said inlet pipe to said outlet pipe passes through said channel, a reference electrode projecting inside said outlet pipe, and a meter for measuring the potential difference between said ring electrode and said reference electrode.

2. The system as defined in claim 1, wherein the internal surface of said ring electrode has noble metal deposited thereon.

3. The system as defined in claim 1, further comprising a source of water containing dissolved hydrogen and a valve for selectively placing said source of water containing dissolved hydrogen in flow communication with said inlet pipe.

4. The system as defined in claim 3, further comprising a sampling line having one end connected to said valve and another end connected to a reactor circuit of a boiling water reactor.

5. The system as defined in claim 1, wherein said metal ring electrode is made of well-oxidized stainless steel.

6. A system for measuring electrochemical corrosion potential comprising an inlet pipe, an outlet pipe, a flow channel tube having one end in flow communication with said inlet pipe and another end in flow communication with said outlet pipe, said flow channel comprising a plurality of spaced metal ring sections and a plurality of spaced ring sections made of electrically insulating material, said metal ring sections and said electrically insulating ring sections being placed in alternating sequence, a reference electrode projecting inside said outlet pipe, a meter for measuring the potential difference between one of said metal ring sections and said reference electrode, and a multiplexer for connecting each of said metal ring sections to said meter sequentially.

7. The system as defined in claim 6, wherein the internal surfaces of said metal ring sections have noble metal deposited thereon.

8. The system as defined in claim 6, further comprising a source of water containing dissolved hydrogen and a valve for selectively placing said source of water containing dissolved hydrogen in flow communication with said inlet pipe.

9. The system as defined in claim 8, further comprising a sampling line having one end connected to said valve and another end connected to a reactor circuit of a boiling water reactor.

10. The system as defined in claim 6, wherein each of said metal ring sections is made of well-oxidized stainless steel.

11. A system for in situ treatment of components of boiling water reactor with metal, said boiling water reactor having a reactor circuit for reactor water flow, comprising:

means for injecting a metal compound into the reactor circuit;

a measurement channel selectively in flow communication with the reactor circuit;

means for diverting a sample of reactor water from the reactor circuit and into said measurement channel, said sample being diverted at a point downstream of said injecting means;

a first test specimen arranged to contact reactor water in said measurement channel;

means for injecting excess dissolved hydrogen into said sample of reactor water;

a reference electrode arranged to contact reactor water in said measurement channel; and a meter for measuring the potential difference between said first test specimen and said reference electrode.

12. The system as defined in claim 11, wherein said first test specimen comprises a ring electrode forming part of said measurement channel.

13. The system as defined in claim 11, further comprising a second test specimen arranged to contact reactor water in said measurement channel, and a multiplexer for connecting said first and second test specimens to said meter in sequence.

14. The system as defined in claim 13, further comprising a first ring section made of electrically insulating material, wherein said first test specimen comprises a second ring section made of electrically conductive material and said second test specimen comprises a third ring section made of electrically conductive material, said second and third ring sections being respectively arranged in flow communication with opposite ends of said first ring section and electrically insulated from each other.

* * * * *